United States Patent [19]

Simms

[11] Patent Number: 4,757,194
[45] Date of Patent: Jul. 12, 1988

[54] METHODS AND APPARATUS FOR SENSING THE MECHANICAL APPLICATION OF FORCE

[75] Inventor: R. John Simms, Palo Alto, Calif.

[73] Assignee: Oxbridge, Inc., Sunnyvale, Calif.

[21] Appl. No.: 917,916

[22] Filed: Oct. 10, 1986

[51] Int. Cl.⁴ .............................................. G01D 5/34
[52] U.S. Cl. ................ 250/227; 250/231 P; 128/780
[58] Field of Search ............... 250/227, 231 R, 231 P; 128/665, 666, 667, 780, 774, 748

[56] References Cited

U.S. PATENT DOCUMENTS

| | | | |
|---|---|---|---|
| 3,215,135 | 11/1965 | Franke | 128/2.05 |
| 3,273,447 | 9/1966 | Frank | 88/1 |
| 3,580,082 | 5/1971 | Strack | 73/406 |
| 4,158,310 | 6/1979 | Ho | 250/231 P |
| 4,210,029 | 7/1980 | Porter | 73/705 |
| 4,487,206 | 12/1984 | Aagard | 128/667 |
| 4,543,961 | 10/1985 | Brown | 128/667 |
| 4,611,600 | 9/1986 | Cohen | 128/667 |

OTHER PUBLICATIONS

Charles M. Davis, "Fiber Optic Sensors: An Overview", Optical Engineering, 24, No. 2: 347–351, (Mar.-/Apr. 1985).

Primary Examiner—David C. Nelms
Assistant Examiner—Khaled Shami
Attorney, Agent, or Firm—Limbach, Limbach & Sutton

[57] ABSTRACT

A probe for sensing the mechanical application of force is described wherein the terminus of at least one optical fiber is provided at a preselected distance from a reflective surface. The reflective surface is reciprocatively mounted relative to the fiber wherein application of steady mechanical force to the reflective surface mounting means causes the reflective surface to move closer to the fiber terminus. A light source and reflected light intensity sensing means are provided. The probe is desensitized to pressure differentials across the fiber terminus-reflective surface distance by providing an atmospheric vent to the space to be sensed. In a preferred embodiment, the catheter-sheathed optical fiber and reflective surface mounting means are used to detect impending incontinence whose onset is signalled to a health care provider by an audible alarm.

9 Claims, 3 Drawing Sheets

U.S. Patent   Jul. 12, 1988   Sheet 1 of 3   4,757,194
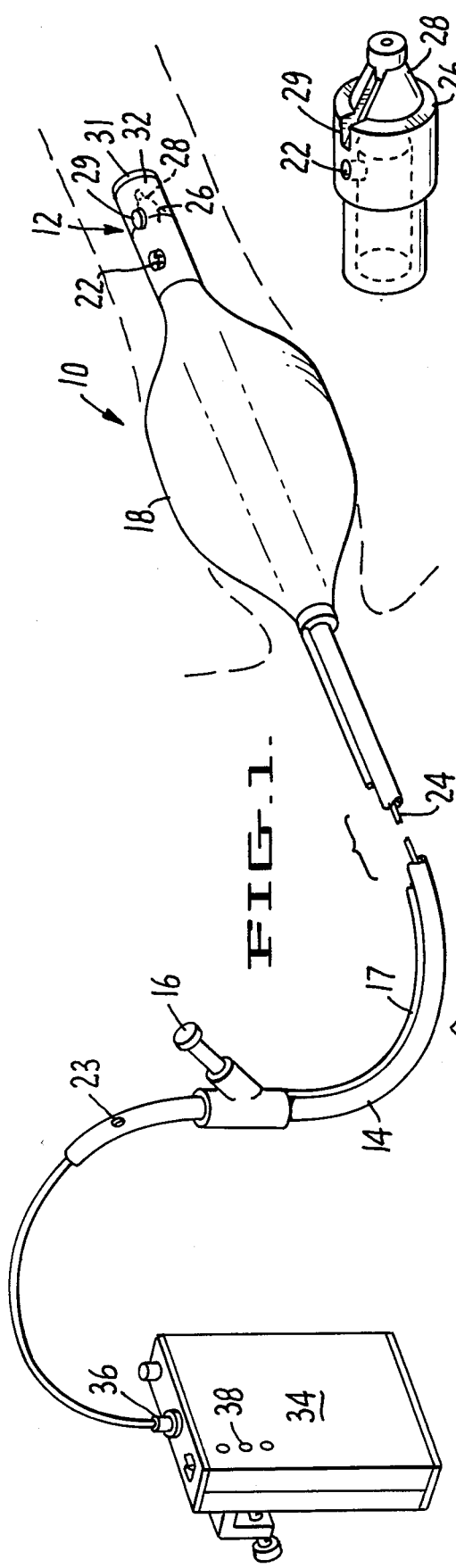
FIG. 1.
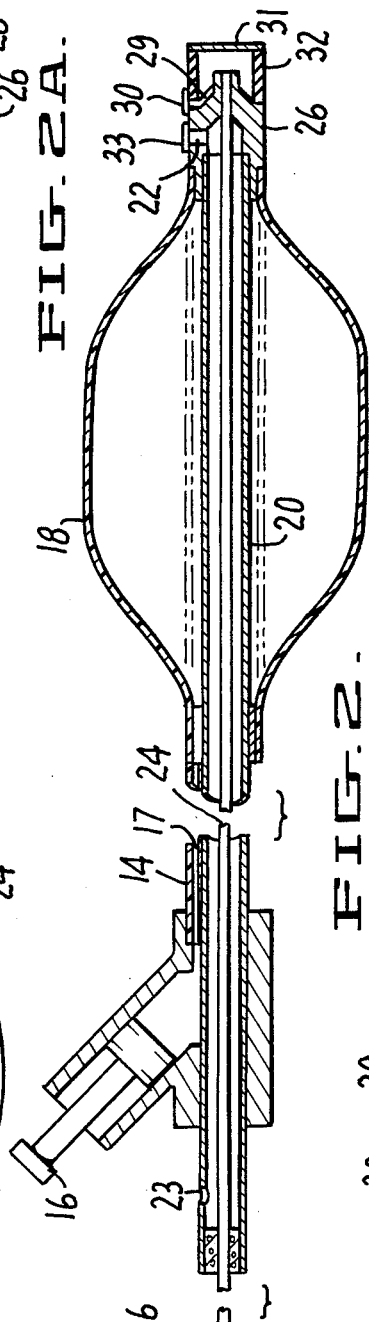
FIG. 2.
FIG. 2A.
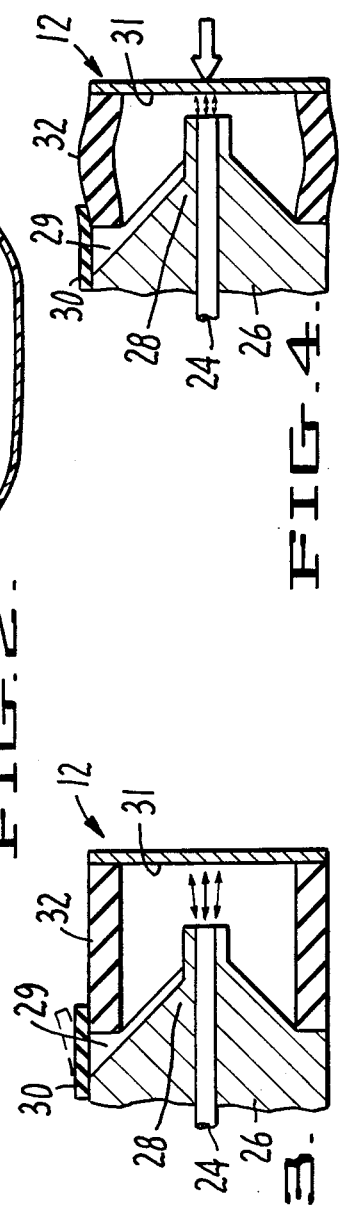
FIG. 3.
FIG. 4.
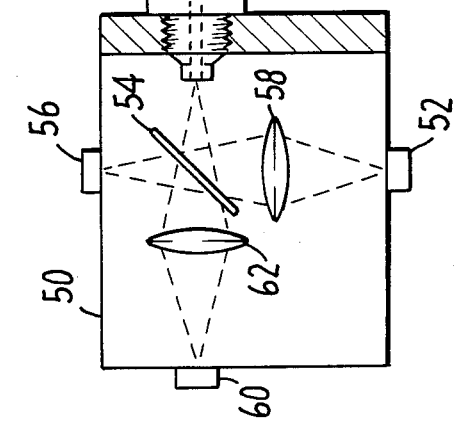

METHODS AND APPARATUS FOR SENSING THE MECHANICAL APPLICATION OF FORCE

TECHNICAL FIELD

This invention relates generally to mechanical force sensing devices, and more particularly to the use of fiber optics to detect the application of mechanical force at the distal end of the fiber along the fiber longitudinal axis.

BACKGROUND OF THE INVENTION

Optical pressure transducers are known for the measurement of intravascular blood pressure and of trans-aortal valve blood pressure. These devices employ a ductile reflecting film which is mounted to respond to extremely small pressure differentials across the reflective film. Small film deformations are sensed and reported. The present invention is specifically provided to avoid the detection of pressure differentials. Rather, the present invention provides a probe which senses only the direct application of mechanical force to the probe tip. It is essentially an object sensor. Pressure differentials, which could accompany the application of mechanical force, are not detected by this sensing device which avoids the creation of pressure differentials by venting the volume between the fiber terminus and the reflective surface to the space to be sensed. The reflective surface or its mounting means only deform when mechanical force is applied to them.

The present invention was developed for a specific application, the sensing and signalling of a patient's impending incontinence. In nursing homes and other clinical settings, patient care is augmented with electronic sensors and alarms which alert the health care provider to patients' physiological conditions. In particular, this device finds application in monitoring patient's impending incontinent episode, sufficiently in advance of the onset of the event so as to allow an attendant to take appropriate action and minimize the effects. While the subject invention is described with reference to this particular probe and method, it will be apparent to those skilled in the art that this description is for purposes of illustration and is not intended to limit the scope of the invention described and claimed herein.

SUMMARY OF THE INVENTION

A probe for sensing the mechanical application of force which comprises an elongate catheter having a proximal vent and a distal vent; at least one optical fiber received within said catheter, said fiber having a source end and a terminus; means for mounting the fiber terminus in the catheter distal end; a reflective surface; means for reciprocatively mounting the reflective surface at a preselected distance from the fiber terminus wherein said reflective surface is enabled to move closer to the fiber terminus, responsive only to the direct, mechanical application of a steady, longitudinally-directed force to the reflective surface mounting means, and to return to said preselected distance upon the removal of the force; means for introducing light to the source end of the optical fiber; means for sensing a reference light intensity; means for sensing the reflected light intensity at the fiber terminus; and signal processing means for creating a detectable signal, said means communicating with both the reference sensing means and the reflective intensity sensing means, wherein said probe is substantially non-responsive to pressure-differentials across the reflective surface and its mounting means.

In certain preferred embodiments, an inflatable, balloon-type catheter is used to fix the position of the catheter in the colon by selectively and reversibly inflating the outer sheath of the catheter.

A method of using the apparatus to detect an impending incontinent episode comprises the steps of providing the above described apparatus; placing the distal, ferrule-end of the catheter in the patient's colon; injecting fluid into the catheter interior tube to thereby increase the catheter sheath outer diameter to temporarily seat the ferrule-end of the catheter in fluid-communicating relationship with the patient's colon; directing light through the optical fiber; determining the magnitude of reflected light intensity when said reflective surface is at a preselected distance from the fiber terminus; contacting said reflective surface mounting means with the impending incontinence; determining the magnitude of the reflected light intensity when said reflective surface is deflected from its preselected distance from the fiber terminus; creating a detectable signal responsive to the comparison of reference and reflected light intensities.

It is an object of this invention to provide a device which senses objects, or the direct application of mechanical force, and is substantially insensitive to pressure differentials between the probe internal volume and the space to be sensed.

It is a further object of this invention to provide a probe which is simply operated, convenient and inexpensive.

It is another object of this invention to provide a sensor which is adaptable to a wide variety of applications.

BRIEF DESCRIPTION OF THE DRAWINGS

FIG. 1 is a perspective view of a preferred embodiment of the instant invention.

FIG. 2 is a partial cross-sectional view of the probe and a schematic view of the optics module of the electronics pack shown in FIG. 1. FIG. 2A is a detailed perspective view of the fiber ferrule.

FIG. 3 is a cross-sectional view of the tip of the probe in the detailed view of FIG. 2.

FIG. 4 is a second cross-sectional view of the tip of the probe under the application of mechanical force.

DETAILED DESCRIPTION OF THE INVENTION

Figure 5:
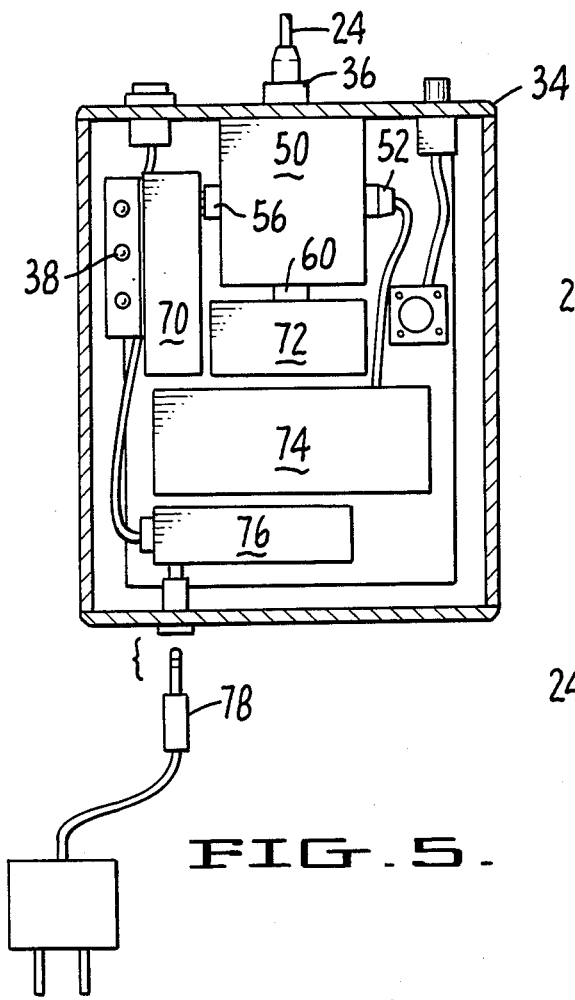
FIG. 5 is a schematic representation of the electronics of the optics and data processing modules of the electronics pack of the preferred embodiment.

A preferred embodiment of the force-sensing probe 10 of the instant invention is shown in FIG. 1. A probe tip 12 is provided at the distal end of an elongate, balloon-type catheter 14. A syringe inlet 16 is provided to inject fluid into an interior tube 17 between outside catheter wall 18 and inside catheter wall 20. The injection of fluid causes the weakened catheter wall 18 to balloon to form a section with an enlarged diameter as seen in FIGS. 1 and 2. In physiological applications, for example, this ballooning catheter can be used to set the probe tip 12 in the appropriate location within a tube, canal, vein or artery. It is within the scope of the invention to use air as the injected fluid. Other fluids might be used depending upon the catheter material of construction and environment in which the catheter and probe are used. In the preferred embodiment, a 16 French Foley catheter, 30 cc balloon from Bard Urological Division of C. R. Bard, Inc., Murray Hill, N.J. is used as the balloon-type catheter 14. The elongate catheter 14 as used in the present invention also contains two vents 22 and 23 near the catheter 14 distal end and proximal end, respectively. The importance of these vents is described more fully below with reference to FIG. 2.

In the preferred embodiment of the invention, a single optic fiber 24 is received within catheter 14. At the catheter distal end, fiber 24 is held in place relative to the catheter 14 by a ferrule 26 through which the fiber 24 passes. The fiber terminus coincides with a ferrule cap 28. The fiber 24 is received by the cap 28 and is affixed to the cap 28 to permit the transmission of light through the fiber 24 and past the cap 28. In a preferred embodiment of the invention, optic fiber 24 is a standard part, POM 1440, made by Poly Optical Products, Inc., Santa Ana, Calif. The ferrule 26 is also available as a standard optical fiber assembly part from AMP of Valley Forge, Pa. The ferrule cap 28 is a conically shaped portion of the ferrule 26. The fiber 24 is received within the interior of the conical cap 28 and is retained in the apical section of the cap 28 by glue. Cap 28 is scored along the conical surface and ring to provide a groove 29 which acts as a distal space vent. In order to achieve a pressure insensitive probe, the volume at the distal end of the fiber 24 must be in communication with the volume to be sensed. The groove 29 is covered over with a hydrophobic, gas permeable membrane 30. This membrane permits equilibration of the external, sensed volume with the internal sensing volume while preventing liquid from entering the distal space which could have deleterious effects upon the measurement of the optical modulation. In the preferred embodiment, Teflon ® (DuPont Co., Wilmington, De.) filter paper available from Gelman Sciences as Teflon ® 450 is used.

Probe tip 12 has a second functional component; reflective surface 31 is held at a preselected distance from the fiber 24 terminus in a reflective surface mounting device 32. In this embodiment, the reflective surface 31 is a mylar film of thickness approximately 0.001 inches; this product is readily available commercially to those skilled in the art. The ductile side walls of the mounting device 32 are made of silicone rubber tubing, which is otherwise untreated but approved for internal human applications. The side walls are sufficiently ductile to deform as shown in FIG. 4. The reflective surface 31 is applied to the distal edges of the silicone rubber tubing and affixed there in place with epoxy glues. This reflective surface mounting device 32, is thus able to maintain the reflective surface 31 at a preselected distance from the fiber 24 terminus, but it is sufficiently ductile to deform upon the application of force at the probe distal end. In this embodiment, that "preselected" distance between the fiber terminus and the reflective surface is equivalent to the length dimension of the silicone rubber tubing used in the mounting device 32. Other means for preselecting a distance are described below. Although not the preferred embodiment, those skilled in the art will recognize the reflective surface 31 can be made sufficiently ductile to deform independently of the side walls of mounting device 32 upon the direct application of mechanical force to the surface 31 along the fiber longitudinal axis and then return to it original position when such force is removed. This mechanism for optical modulation of the distance is intended to be within the scope of the claims appended hereto. Thus, the reflective surface 31 is reciprocatively mounted relative to the fiber 24 terminus (FIG. 3), reciprocating between a first position located at a preselected distance from the fiber terminus, a second position at a distance closer to the fiber terminus after deforming force is applied to the reflective surface mounting means 32 (FIG. 4) and then returning to the initial position at a preselected distance from the fiber terminus. Other means for mounting the reflective surface 31 relative to the fiber terminus are more fully described below with reference to FIGS. 6, 7, 8 and 9.

Another important aspect of the probe tip 12 relates to the distal vent 22 and proximal vent 23. In prior art devices, it is taught to measure pressure differentials across the reflective surface 31 by isolating the volume behind the surface 31 from the pressure at the location to be sensed. Pressure responsive, ductile films and optical sensing means were provided to detect small deformations in the film caused by pressure differentials across the reflective surface. In the instant invention, the internal catheter volume is vented to the atmosphere through vents 22 and 23. As described above with reference to the groove 29 and membrane 30, another membrane 33 is provided to cover the distal vent 22 and prevent liquids from entering the catheter 14. The same materials which are useful for membrane 30 are equally useful for membrane 33. It is important for the distal vent 22 to be near the probe tip 12, certainly nearer the distal end than the ballooning section of the catheter. It is important for the vent 22 to be located in, or very near to the volume to be sensed to permit rapid equilibration of pressure between the distal volume between the reflective surface 30 and fiber terminus, and the volume to be sensed as well as the catheter interior volume and the volume to be sensed. Otherwise, a false positive signal could be generated if a sudden shift in prevailing pressure on the distal side of the balloon was not promptly communicated through the vent 22. In combination, this distal vent 22, and corresponding ferrule aperture 29, desensitize the instant probe from responding to pressure differentials across the reflective surface 31. In the preferred embodiment of the invention, when used to detect impending incontinence, the distal vent 22 also specifically serves to pass intestinal gas which must be permitted to pass by the probe 10 to insure patient comfort and health. Other embodiments which are also substantially pressure insensitive are described more fully below with reference to FIGS. 6, 7 and 8.

At the proximal end of the catheter 14 the optical fiber is fastened to and optically connected to an electronics pack 34 via probe connection 36. In the preferred embodiment, injection-molded parts available from AMP, Valley Forge, Pa. are used to mate the source end of the optical fiber 24 with an optics module contained within the electronic pack 34. Preferably, a conical ferrule is provided at the source end of the fiber 24 to mate with a conical ferrule provided within the optics module. Various mating relationships are possible, but the mating members from AMP "splice" the source end of the optical fiber into the optics module by surface contacting the caps of ferrules.

The external surface of electronics pack 34 is provided with an alarm light 38 which signals the application of force to the distal end of catheter 14, at probe tip 12.

In the preferred embodiment in which a single optical fiber is used, the optical modulation, sensing and signalling techniques are described with reference to FIGS. 2, 3 and 4. It will be apparent to those skilled in the art that similar procedures can be used in conjunction with multiple optical fibers, which embodiments are clearly intended to fall within the scope of claims herein. The optics module 50 is provided within the electronics pack 34. Within the optics module 50, there is a light source 52 which is directed towards a beam splitter 54. The beam splitter 54 is angled such that a portion of the light emanating from the source 52 is directed towards the source end of optical fiber 24 while another portion of the light passes through the beam splitter 54 and impinges upon a reference detector 56. A source lens 58 is provided in the source light path to focus some of the light from source 52 at the reference detector 56 and at the source end of fiber 24.

In the preferred embodiment, a light emitting diode is used as the source 52. One such LED is manufactured by Oshino, #OCRA-150-C, available from Wamco, Inc., Fountain Valley, CA. In order to improve the battery lifetime, the LED circuit can be pulsed to provide, for example, light for 0.1 seconds once every five seconds. Other light sources are possible which would be known to those skilled in the art.

While the source 52, beam splitter 54 and reference detector 56 account for providing light to the distal end of the probe 10, a signal detector 60 and detector lens 62 are provided to measure the magnitude of the reflected light intensity. At steady state, when no force is being applied to the distal end of the probe, the magnitude of the reflected light intensity is represented by $R_0$. When longitudinal force is applied to the probe, there is a change in the reflected light intensity (now $R_1$) resulting from deflection of the reflective surface 30 from its preselected distance away from the fiber terminus. This reflected light intensity is ratioed against the source signal magnitude $S_0$. The instrument is designed to sound an alarm when the sensed ratio $R_1/S_0$ differs by more than ten percent from the steady state signal $R_0/S_0$. This is more aptly seen in FIGS. 3 and 4, which detail the physical modulation of the distance between the reflective surface 30 and the fiber terminus. Sensing occurs by creating a signal which differs from the steady state signal. When the probe 10 is at rest, with no deflection of the reflective surface 30 from its preselected distance, light from the source 52 reflects off the beam splitter 54 into the fiber 24 and thereafter emanates from fiber 24 at the distal end of the probe 10. The light emanating from fiber 24 at the distal end diverges and then impinges upon the reflective surface 30. A certain amount of light is reflected back towards the fiber 24, known as the reflected light intensity ($R_0$). This signal then travels back through fiber 24 towards the proximal end of probe 10. The reflected light emanates from the proximal end of fiber 24, passes through both the beam splitter 54 and the detector lens 62 and is sensed at the signal detector 60 as $R_0$. A ratio is electronically established relating the magnitude of the intensity of light sensed at the reference detector 56 ($S_0$) to the magnitude of reflected light intensity ($R_0$) sensed at the signal detector 60. This first ratio is the steady state signal $R_0/S_0$. When the reflective surface 30 is perturbed from its preselected distance, the divergence of the light emanating from the fiber 24 remains unchanged, but the magnitude of the light intensity reflected back onto the fiber terminus changes due to a modulation of the distance between the reflective surface and the fiber. The change in the magnitude of the reflected light intensity is sensed at the fiber terminus, transmitted through to the optics module 50 and detected at the signal detector 60 as $R_1$. The change in the reflected light intensity detected at signal detector 60 changes the ratio of the source to signal intensities $R_1/S_0$. This change from the steady state ratio $R_0/S_0$ to a new ratio $R_1/S_0$ activates an alarm in the electronics pack 34.

Another embodiment for optically detecting changes in the fiber terminus to reflective surface distance involves the use of an optical Y-tap to split the light travelling from the source to the fiber and the light returning from the fiber to detection. One such system is described in "Fiber Optics Sensors: An Overview," Charles M. Davis, 24 Optical Engineering 347–51, March/April 1985. In this article, it is suggested to provide a source and a photodetector on the "prongs" of the "Y" while providing a reflective surface at the base of the fiber "Y". Thus, light from the source is transmitted through a Y-tap into the sensor fiber, propagates down the sensor fiber and exits from its end. The light that exits the fiber propagates through the medium separating the fiber from the reflecting surface, reflects from that surface, and propagates back toward the fiber. A fraction of the reflected light, depending on the change in distance from the fiber to the reflective surface is reintroduced into the fiber and propagates to the Y-tap, where it is divided between the source and detector fiber. The latter portion is photodetected. As in the optics module 50, described with reference to the preferred embodiment, the change in the magnitude of the reflected light intensity due to a modulation in the distance between the fiber terminus and the reflective surface causes a change in the ratio which can be detected and reported.

The details of the electronics pack 34 are shown schematically in FIG. 5. Fiber 24 enters pack 34, through a connector 36, and communicates with the optics module 50 just described. Light source 52 is connected to a digital interface circuit 74. This circuit is provided to pulsitize the source light, for example, to provide light for 0.1 seconds and then 5 seconds off. The reference detector 56 is connected to a source preamplifier circuit 70 to generate an output voltage. The signal detector 60 is connected to a signal preamplifier circuit 72 to generate another output voltage. The preamplifier output voltages are ratioed to create a steady state ratio and a sensed ratio. Deviations of more than ten percent from the steady state ratio can be signalled or alarmed. One circuit which would accomplish this task provides a comparator for receiving the detector output voltages. When there is no deflection, a threshold ratio can be set. The comparator can be instructed to provide a detectable signal when the ratio deviates more than ten percent of the threshold ratio. Other more complex circuits can be provided which are well known to those skilled in the art and are intended to be within the scope of this invention.

Power is provided to electronics pack 34 through a plug-in power supply 78, preferably an easily replaced battery module. A wall charger unit which is UL rated for hospital use can be provided to recharge the battery pack. In the preferred, incontinent episode sensing device, the power pack should be sufficiently light and compact to permit its ambulatory use in paraplegic and quadriplegic patients. The pulsitized LED light source described above permits extended periods of clinical use without need for frequent power supply recharging or replacement.

Figure 6A:
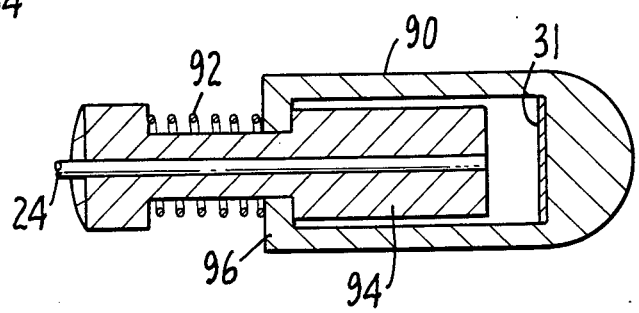
FIG. 6A is a side elevational view of an alternate design for the film mounting means of the present invention.
Figure 6B:
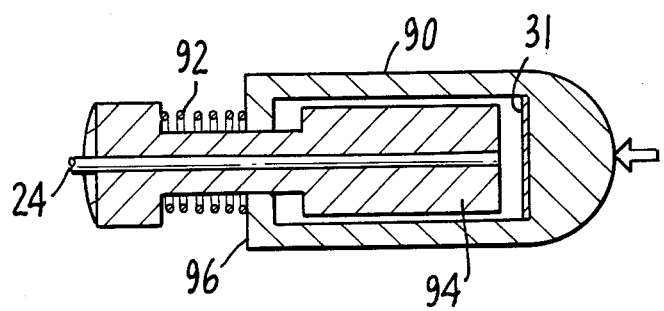
FIG. 6B is the same cross-sectional view under the application of mechanical force.

Alternate embodiments for the reflective surface mounting means are conceived as follows. Referring to FIG. 6A, sensor tip 90 has a bullet-like overall shape with a blunted, round tip at the distal end of the probe. The interior surface of the tip 90 is a substantially cylindrical cavity for receiving the fiber ferrule 94. At the proximal end of the sensor tip 90, there is a collar 96 which necks down to receive the fiber ferrule 94 and which serves as a surface for interacting with a spring 92. The fit between the fiber ferrule 94 and the collar 96 must be sufficiently loose to permit gas to leak out of the volume between the fiber terminus and the reflective surface 31. This venting renders the probe substantially pressure insensitive. As shown in FIG. 6B, when a longitudinally-directed force (represented by the arrow) is applied to the tip 90, the spring 92 is compressed and the reflective surface 31 is moved closer to the fiber terminus, thus introducing a change in the magnitude of reflected light intensity at the fiber terminus. This distance/intensity modulation is then converted to a detectable signal through the optics module and electronics described above. Removal of the longitudinally-directed force causes the spring 92 to expand to its original position.

Figure 7A:
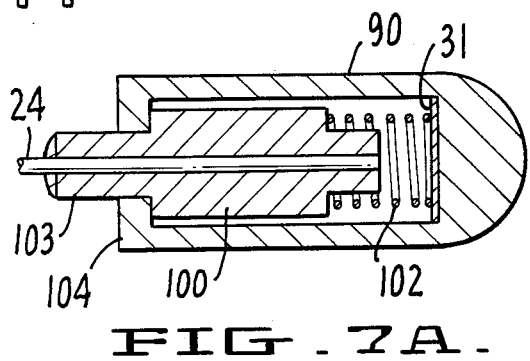
FIG. 7A is a side elevational view of a second alternate design for the film mounting means of the present invention.
Figure 7B:
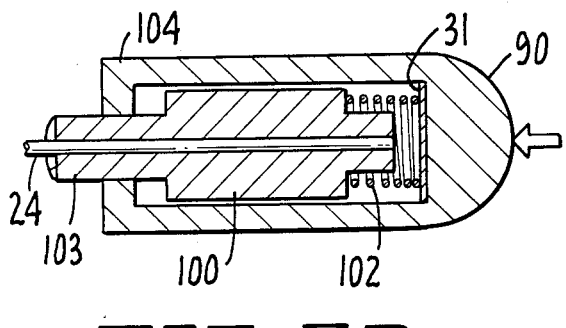
FIG. 7B is the same cross-sectional view under the application of mechanical force.

Referring now to the sensor tip 90 shown in FIG. 7A and 7B, the sensor tip 90 is provided in essentially the same external and internal shape as the embodiment described above with reference to FIGS. 6A and 6B. However, the fiber ferrule 100 of this embodiment has a cap section at its distal end, that cap end having a smaller outer diameter than the balance of the ferrule 100. In the annular space between the cap end and the sensor tip 90 inner surface is provided a spring 102 which sets the reflective surface 31 at a preselected distance from the fiber terminus and which can reciprocate between this position and the compressed position shown in FIG. 7B. Removal of the longitudinal force represented by the arrow will cause the spring 102 to expand and return to the steady state position. The fit between the sensor tip 90 internal surface and the fiber ferrule 100 and between the fiber sheath 103 and sensor tip collar 104 must be sufficiently loose to permit gas to leak out of the volume between the reflective surface 31 and the fiber ferrule 100.

Figure 8:
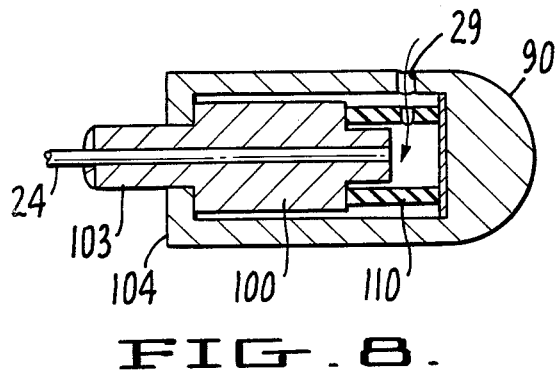
FIG. 8 is a side elevational view of a third alternate design for the film mounting means of the present invention.

FIG. 8 discloses another embodiment, which is similar in effect to the device shown in FIG. 7. The fiber ferrule 100 has the same capped end and the sensor tip 90 is substantially the same as shown in FIGS. 6 and 7. In this embodiment, however, flexible spring means 110 are provided which have the effect of isolating the distal volume between the reflective surface 31 and the fiber terminus from the space to be sensed. Consequently, a vent 29 is provided through the sensor tip 90 wall and through the side wall of the flexible spring means 110. One embodiment of the flexible spring means 110 is the silicon rubber tubing described above with reference to the preferred embodiment of the invention. Again, the fit between the sensor tip 90 internal surface and the fiber ferrule 100 and between the fiber sheath 103 and the collar 104 must be sufficiently loose to permit gas to easily leak out of the distal volume.

Figure 9:
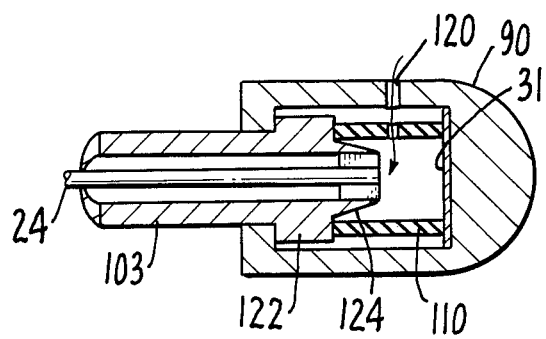
FIG. 9 is a side elevational view of a fourth alternate design for the film mounting means of the present invention.

FIG. 9 shows yet another sensor tip 90 having the same overall bullet-like shape as embodiments described with reference to FIGS. 6, 7 and 8. It will be noted, however, that the overall length of the sensor tip 90 is shorter than the other embodiments thus far described. In this embodiment, the conically-tipped (124) cylindrical (103) ferrule 122 is provided to fit within the sensor tip 90 internal surface. As in the embodiment shown in FIG. 8, this embodiment provides a flexible spring means 110 through which is provided a distal space vent 120 which also passes through the sensor tip 90 wall. This vent permits the distal volume between the fiber terminus and the reflective surface 31 to communicate with the space to be sensed. Tip 90 is provided to slide on the cylindrical section 103 of the ferrule 122.

In the preferred method of the instant invention, relating to the early detection of an impending incontinent episode, an apparatus such as described with reference to FIG. 2 is first provided. Subsequently, the distal end of the probe 10 is inserted into the patient's anus and positioned approximately three to five inches inward in the colon. Next, a syringe is attached to the syringe inlet 16. Air is then forced into the internal tube 17 causing the balloon to form in outside catheter wall 18, thereby reversibly fixing the position of the probe 10 within the patient's colon. Assuming that the battery pack provides sufficient power to the source light and optics module, the probe will remain quiescent until incontinence approaches and deflects the reflective surface 31 from its steady state position. Ideally, an audible alarm will be provided which tends towards the melodic so as not to be unpleasant to the patient or health care provider.

EXAMPLE I

Figure 10:
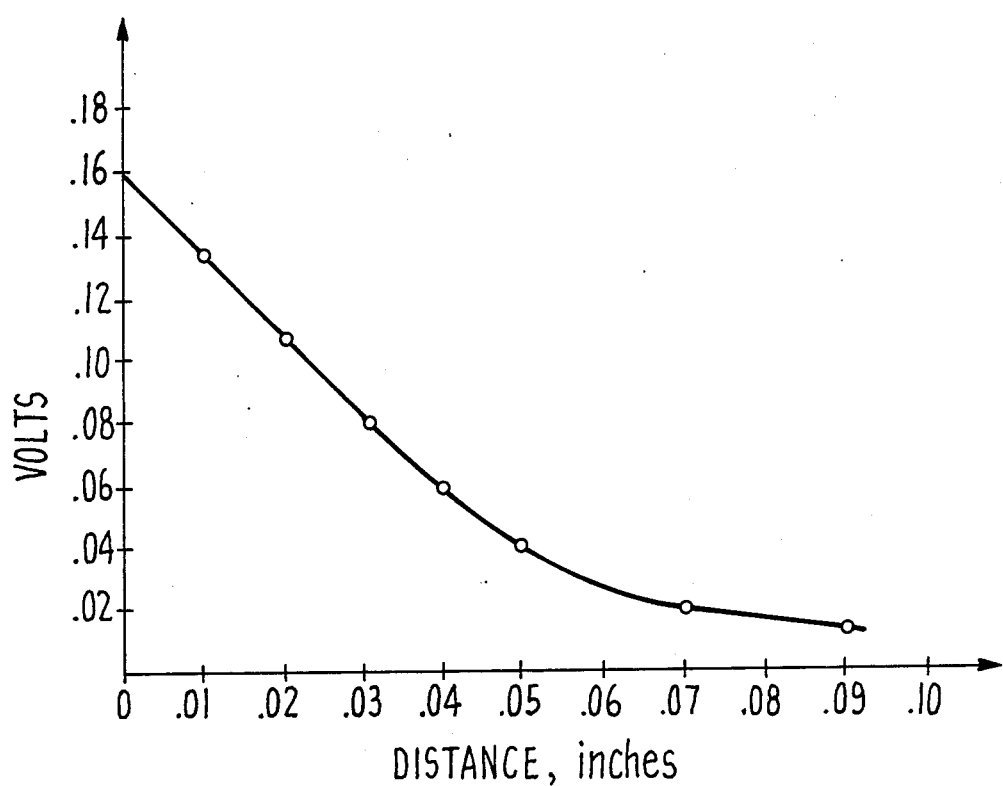
FIG. 10 is a plot of experimental data showing signal detector output voltage versus the fiber-film distance.

To demonstrate the modulation of detected light intensity, recorded as voltage, an apparatus was constructed using an optical fiber and a reflective mylar film as disclosed in reference to the preferred embodiment. FIG. 10 is a plot of the output voltage at the signal detector versus the distance between the reflective film and the optical fiber. This plot shows clearly that the reflected light intensity increases as the film moves closer to the fiber terminus.

I claim:
1. A probe for sensing the mechanical application of force which comprises
    an elongate catheter, having a proximal vent and a distal vent;
    at least one optical fiber, received within said catheter, said fiber having a source end and a terminus;
    means for mounting the optical fiber terminus in the catheter distal end;
    a reflective surface;

means for reciprocatively mounting the reflective surface at a preselected distance from the optical fiber terminus wherein said reflective surface is enabled to move closer to the fiber terminus, responsive only to the direct, mechanical application of a steady longitudinally-directed force to the reflective surface mounting means, and to return to said preselected distance upon the removal of the force;

means for introducing light to the source end of the optical fiber;

means for sensing a reference light intensity;

means for sensing the reflective light intensity at the fiber terminus; and, signal processing means for creating a detectable signal, said signal processing means communicating with both the reference sensing means and the reflected light intensity sensing means, wherein said probe is substantially non-responsive to pressure-differentials across the reflective surface and its mounting means.

2. A probe as in claim 1 wherein said catheter distal vent is covered by a hydrophobic, gas permeable membrane.

3. A probe as in claim 1 wherein the fiber mounting means comprises a vented ferrule having a substantially conical tip section, said optical fiber mounted along the altitude of said ferrule conical section, said ferrule conical section having a groove in the surface to act as a vent, the fiber terminus within said ferrule being substantially coincident with the apex of said ferrule conical section, and said fiber mounting means having a cylindrical base section for receiving said optical fiber and containing an aperture therethrough to vent the internal catheter volume at the catheter distal end, said cylindrical base aperture aligning with said elongate catheter distal vent; and, the reflective surface mounting means comprises a cylindrical member, having ductile curved surfaces, which is sealed to, and fastened over, the ferrule conical section, the distal basal surface of said cylindrical member comprising the reflective surface which is thereby reciprocatively maintained at a preselected distance from, and facing the fiber terminus, wherein said groove in the ferrule surface vents the volume between the fiber terminus and the reflective surface to the atmosphere prevailing at the probe distal end.

4. A probe as in claim 1 wherein the fiber mounting means comprises a substantially cylindrical ferrule whose distal basal surface is coincident with the fiber terminus;

the reflective surface mounting means comprises an elongate, blunted tip having a distal, rounded exterior surface and a cylindrically-shaped interior surface adapted to receive and fully contain the ferrule, wherein said reflective surface is mounted on the cylindrically-shaped interior basal distal surface of said elongate, blunted tip and said reflective surface lies in a plane perpendicular to the optical fiber longitudinal axis; and, spring means, located between the catheter and the near end of the blunted tip, biasing the tip away from the catheter, for reciprocatively positioning the reflective surface relative to the fiber terminus, said spring means responsive to the application of mechanical force to said blunted tip distal end along the optical fiber longitudinal axis.

5. A probe as in claim 1 wherein the fiber mounting means comprises a ferrule which terminates in a cap section having a diameter smaller than said ferrule, the fiber terminus optically communicating through said cap;

the reflective surface mounting means comprises an elongate, blunted tip having a distal, rounded exterior surface and a ferrule-receiving and ferrule-containing interior surface, wherein said reflective surface is mounted on the distal interior surface of said elongate, blunted tip and said reflective surface lies in a plane perpendicular to the optical fiber longitudinal axis; and, spring means, located between the ferrule cap section outer surface and the distal interior surface of said elongate, blunted tip, to bias said elongate, blunted tip away from the optical fiber terminus, wherein said spring means is responsive to the application of mechanical force to said blunted tip distal end in the direction of the optical fiber longitudinal axis.

6. A probe as in claims 1, 2, 3, 4 or 5 wherein said elongate catheter contains an interior tube and the outer sheath of the catheter has a variable wall strength, whereby theh diameter of a section of the catheter near the fiber terminus can be selectively and reversibly enlarged by the injection of fluid into the interior tube.

7. A probe for sensing the mechanical application of force to a tip which comprises:

an elongate catheter having a proximal vent and a distal vent, which contains an interior tube and an outer sheath, said sheath having a variable wall strength, whereby the diameter of a distal section of the catheter can be selectively and reversibly enlarged by the injection of fluid into the interior tube;

at least one optical fiber, received within said catheter, having a source end and a terminus;

a vented ferrule having a substantially conical tip section and a cylindrical base section, said optical fiber mounted along the conical section altitude, the optical fiber terminus being substantially coincident with the apex of said ferrule conical section, said conical section having a groove in the surface to act as a vent, and said ferrule cylindrical base section receiving said optical fiber and containing an aperture therethrough to vent the internal catheter volume at the catheter distal end, said ferrule cylindrical base aperture aligning with said catheter distal vent;

a reflective surface;

reflective surface mounting means comprising a cylindrical member, having ductile curved surfaces, which is sealed to, and fastened over, said vented ferrule conical section, the distal basal surface of said reflective surface mounting means cylindrical member comprising the reflective surface which is thereby reciprocatively maintained at a preselected distance from, and facing the optical fiber terminus;

means for introducing light to the source end of the optical fiber;

means for sensing a reference light intensity;

means for sensing the reflected light intensity at the optical fiber terminus; and signal processing means for creating a detectable signal, said means communicating with both the reference sensing means and the reflected intensity sensing means, whereby said probe is rendered responsive only to the direct mechanical application of a steady, longitudinally-directed force along the optical fiber axis and wherein said probe is substantially nonresponsive to pressure differentials across the reflective surface and its mounting means.

8. Method for detecting steady axial force which comprises the steps of:

(a) providing a probe for detecting force comprising an elongate catheter having a proximal vent and a distal vent; at least one optical fiber received within the catheter having a source end and a terminus; means for mounting the optical fiber terminus in the catheter distal end; a reflective surface; means for reciprocatively mounting the reflective surface at a preselected distance from the optical fiber terminus whereby said reflective surface is enabled to move closer to the fiber terminus, responsive only to the direct, mechanical application of a steady longitudinally directed force to the reflective surface mounting means, and to return to said preselected distance upon the removal of the force; means for introducing light to the source end of the optical fiber; means for sensing a reference light intensity; means for sensing the reflected light intensity at the fiber terminus; and, signal processing means for creating a detectable signal, said signal processing means communicating with both the reference sensing means and the reflected light intensity sensing means;

(b) directing light through the optical fiber;

(c) determining the magnitude of reflected light intensity when said reflective surface is at a preselected distance from the optical fiber terminus;

(d) applying longitudinally directed mechanical force to the reflective surface mounting means;

(e) determining the magnitude of reflected light intensity when said reflective surface is deflected from its preselected distance from the optical fiber terminus;

(f) comparing the magnitude of the signal generated in step (c) with the signal generated in step (e); and, (g) creating a detectable signal responsive to the comparison of light intensities.

9. A method of determining impending incontinence in a patient which comprises the steps of:

(a) providing an elongate catheter having a distal vent and a proximal vent, which contains an interior tube and an outer sheath, said outer sheath of the catheter having a varaible wall strength, whereby the diameter of a distal section of the catheter can be selectively and reversibly enlarged by the injection of fluid into the interior tube; at least one optical fiber, received within said catheter, having a source end and a terminus; a vented ferrule having a substantially conical tip section and a cylindrical base section, optical fiber mounted along the conical section altitude, the optical fiber terminus being substantially coincident with the apex of said ferrule conical section said ferrule conical section having a groove in the surface to act as a vent, ferrule cylindrical base section receiving said fiber, and containing an aperture therethrough to vent the internal catheter volume at the catheter distal end, said ferrule cylindrical base aperture aligning with said catheter distal vent; a reflective surface; reflective surface mounting means comprising a cylindrical member, having ductile curved surfaces, which is sealed to, and fastened over, said vented ferrule conical section, the distal basal surface of said reflective surface mounting means cylindrical member comprising the reflective surface which is thereby reciprocatively maintained at a preselected distance from, and facing the optical fiber terminus; means for introducing light to the source end of the optical fiber; means for sensing a reference light intensity; means for sensing the reflected light intensity at the optical fiber terminus; and, signal processing means for creating a detectable signal said signal processing means communicating with both the reference sensing means and the intensity sensing means;

(b) placing the distal, ferrule-end of the catheter in the patient's colon;

(c) injecting fluid into said catheter interior tube to thereby increase the catheter sheath outer diameter to temporarily seat the ferrule-end of the catheter in fluid-communicating relationship with the patient's colon;

(d) directing light through the optical fiber;

(e) determining the magnitude of reflected light intensity when said reflective surface is at a preselected distance from the optical fiber terminus;

(f) contacting said reflective surface mounting means with the impending incontinence;

(g) determining the magnitude of reflected light intensity when said reflective surface is deflected from its preselected distance from the fiber terminus;

(h) comparing the magnitude of the signal generated in step (e) with the signal generated in step (g); and, (i) creating a detectable signal responsive to the comparison of light intensities.

* * * * *